(12) United States Patent
Kern et al.

(10) Patent No.: US 10,131,946 B1
(45) Date of Patent: Nov. 20, 2018

(54) METHOD FOR IDENTIFYING AGENTS REGULATING LIPOFILLING ACTIVITY

(71) Applicant: NSE Products, Inc., Provo, UT (US)

(72) Inventors: Dale Kern, Provo, UT (US); Jin Namkoong, Provo, UT (US)

(73) Assignee: NSE Products, Inc., Provo, UT (US)

( * ) Notice: Subject to any disclaimer, the term of this patent is extended or adjusted under 35 U.S.C. 154(b) by 0 days.

(21) Appl. No.: 14/704,880

(22) Filed: May 5, 2015

Related U.S. Application Data

(60) Provisional application No. 61/988,784, filed on May 5, 2014.

(51) Int. Cl.
*C12Q 1/68* (2018.01)
*C12Q 1/6876* (2018.01)

(52) U.S. Cl.
CPC ..... *C12Q 1/6876* (2013.01); *C12Q 2600/148* (2013.01); *C12Q 2600/158* (2013.01)

(58) Field of Classification Search
CPC .................................................. C12Q 1/6876
USPC .......................................................... 506/9
See application file for complete search history.

(56) References Cited

U.S. PATENT DOCUMENTS

| | | | | |
|---|---|---|---|---|
| 2005/0008621 A1* | 1/2005 | Kirkland | ............... | C12N 5/0667 424/93.21 |
| 2006/0034542 A1* | 2/2006 | Aoyama | ............ | G06K 9/00275 382/276 |
| 2008/0025931 A1* | 1/2008 | Pelletier | ................. | A61K 8/602 424/59 |
| 2009/0291066 A1* | 11/2009 | Pappas | ..................... | A61K 8/49 424/93.7 |

OTHER PUBLICATIONS

Crandall et al., Endocrinology, 140:154-8 (Year: 1999).*

* cited by examiner

*Primary Examiner* — Karla A Dines
(74) *Attorney, Agent, or Firm* — Thorpe North & Western, LLP; David W. Osborne (57) ABSTRACT

A method is provided for characterizing a lipofilling agent causing increased lipofilling activity in adipose tissue from a target body area. Such a method can include obtaining a plurality of distinct preadipocyte cultures taken from a plurality of distinct body areas of an individual, exposing the plurality of distinct preadipocyte cultures to a plurality of potential lipofilling agents, culturing the plurality of distinct preadipocyte cultures through differentiation to form a plurality of distinct adipocyte cultures, measuring a degree of lipofilling activity of adipocytes from each of the plurality of distinct adipocyte cultures, and quantifying the measured lipofilling activity across the plurality of distinct adipocyte cultures to identify a lipofilling agent causing increased lipofilling activity in adipose tissue from the target body area as compared to adipose tissue in the non-target body area.

11 Claims, 4 Drawing Sheets

METHOD FOR IDENTIFYING AGENTS REGULATING LIPOFILLING ACTIVITY

PRIORITY DATA

This application claims the benefit of U.S. Provisional Patent Application Ser. No. 61/988,784, filed on May 5, 2014, which is incorporated herein by reference.

BACKGROUND

Human skin aging occurs at different rates, with some individuals showing fewer signs of aging than others, despite variations in environmental conditions. Current corrective measures mainly focus on smoothing the surface microtexture of the skin, decreasing perceived pigmentation irregularities, and reducing the appearance of lines and wrinkles. For deeper lines, wrinkles, and macro folds of the skin, the use of fillers has come into common use. The upper and lower thirds of the face, along with the neck, have received the most attention, with procedures now being developed for the midfacial areas. Injectable fillers and stimulators are used mainly to replace volume in an aging face, commonly with autologous fat transfer and grafting. Enrichment of grafts for adipocyte-derived stem cells is now seen as a step toward better long-term success; however, given their multipotent nature, a certain degree of caution may be needed in attempting to stimulate differentiation for enhancement of adipocyte number and lipid accumulation.

In addition to filling voids in the face, a comprehensive anti-aging approach can include resurfacing with chemicals, lasers, and microdermabrasion, as well as stimulating the restructuring of the extracellular matrix with topical active ingredients and energy sources such as thermal, light, ultrasound and radiofrequencies. Methods developed to document the aging face primarily focus on the shape, color and texture of the facial skin and its thickness. However, one aspect of aging facial skin remaining to be adequately targeted is pan-facial subcutis lipoatrophy (FIG. 1), or the loss of bulking supportive fat lying beneath the dermis in general.

DETAILED DESCRIPTION OF EMBODIMENTS

Before the present disclosure is described herein, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Comparative terms such as "more effectively," "greater than," "improved," "enhanced," and like terms can be used to state a result achieved or property present in a formulation or process that has a measurably better or more positive outcome than the thing to which comparison is made. In some instances comparison may be made to the prior art.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the terms "comprises," "comprising," "containing," "having," and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly, and vice versa.

As used herein, compounds, formulations, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a concentration range of 0.1 to 5 ng/ml should be interpreted to include not only the explicitly recited concentration limits of 0.1 ng/ml and 5 ng/ml, but also to include individual concentrations such as 0.2 ng/ml, 0.7 ng/ml, 1.0 ng/ml, 2.2 ng/ml, 3.6 ng/ml, 4.2 ng/ml, and sub-ranges such as 0.3-2.5 ng/ml, 1.8-3.2 ng/ml, 2.6-4.9 ng/ml, etc. This interpretation should apply regardless of the breadth of the range or the characteristic being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

Figure 2:
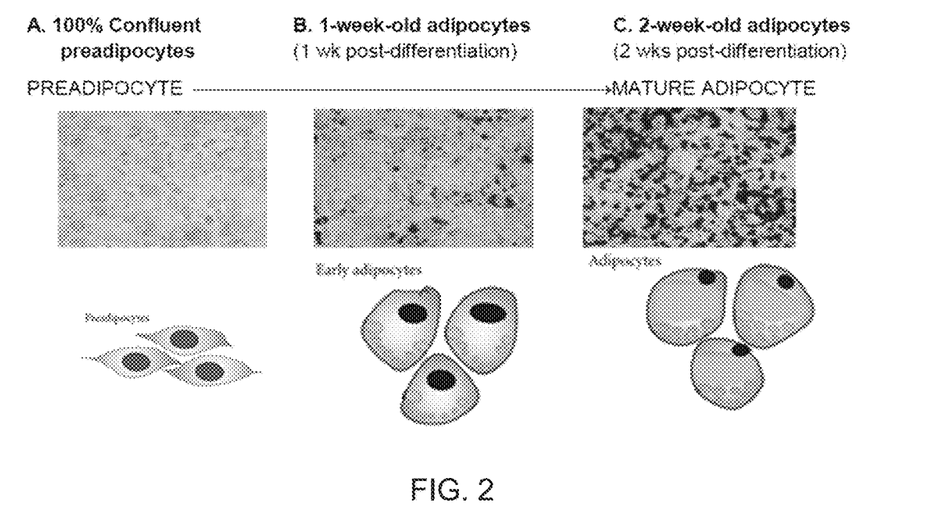
FIG. 2 shows images and a graphical representation of lipofilling of preadipocytes according to one aspect of the present disclosure.

Generally, adipocytes (adipose cells) are cells that internally store lipids such as triglycerides (e.g. triacylglycerol) in a process called lipofilling or lipid accumulation. Adipocytes have a developmental origin from the mesoderm, and arise through the differentiation of preadipocytes. These cells grow in size as the storage volume of lipid increases. For the purposes of the present disclosure, the term "adipocyte" refers to fully differentiated adipocyte cells and to cells that develop into adipocytes. In one non-limiting example, adipocyte can include preadipocyte to adipocyte cells. Lipofilling can thus occur in preadipocytes, maturing adipocytes, and mature adipocytes. One example of lipofilling activity is depicted in FIG. 2, which shows preadipocyte cells maturing into adipocytes over time, and the resultant accumulation of lipid (shown dark spots). The accumulation of lipid is depicted graphically in the bottom row of FIG. 2. It is noted that the term "lipofilling activity" is generally described herein as an increase in lipid accumulation in an adipocyte cell; however, "lipofilling activity" can also refer to a decrease in lipid accumulation, whereby lipofilling is inhibited or otherwise down-regulated.

Figure 1:
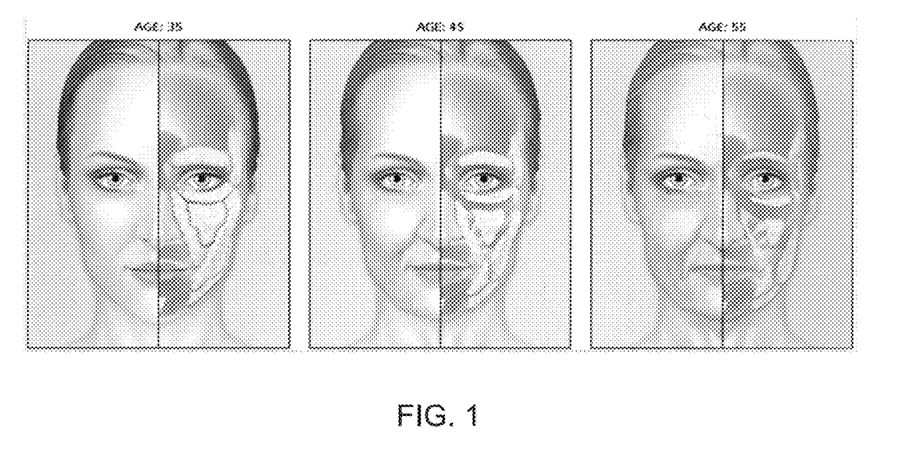
FIG. 1 shows a graphical representation of the change in supportive fat beneath the dermis as a function of age.

Adipocytes reside in connective tissue referred to as adipose tissue, which can include several subtypes such as white, brown, beige, and pink adipose tissue. Of these, white adipose tissue is the form of adipose tissue associated with energy storage, or in other words, with body fat. While such adipose tissue and the associated adipocytes are often thought of as primarily an energy storage system, other rolls such as cushioning, thermal insulation, and the like are apparent. Additionally, the degree of lipid accumulation in adipocytes can provide visual cues to others as to the fitness, age, gender, and the like of a subject. As one example, loss of supportive fat beneath the dermis in the face can present a visual cue related to aging, as is shown in FIG. 1. While the supportive fat in the face generally decreases with age, weight loss can also reduce supportive fat, resulting in a chiseled or aged look in younger subjects.

As such, increasing the lipofilling activity in adipocytes associated with the face can rebuild such supportive fat, and thus present a more youthful appearance. It is additionally contemplated that an increase in lipofilling activity can function to maintain facial supportive fat through advancing age, weight loss, or any other factor that would normally result in facial fat loss. Furthermore, a targeted increase in lipofilling activity in specific body areas can be additionally beneficial, as a general increase in adipocyte fat accumulation throughout the body may be undesirable.

Additionally provides a methodology for identifying and characterizing compounds and compound compositions that affect or otherwise regulate lipofilling activity, in some cases targeted to specific anatomical sites and/or associated with certain age groups of subjects. Compounds can be quantified in terms of their individual lipofilling activities, as well as the combined lipofilling activities of combinations of compounds. As such, the present disclosure additionally provides methods and systems for identifying compounds, active ingredients, and the like, that regulate lipofilling activity in a cell, as well as providing detailed quantification of such compounds. Furthermore, aspects of the present technology provide for identifying and characterizing compounds that regulate lipofilling by cell type and/or body area, such as, for example, adipocyte cells in the face as opposed to the thighs. Such regulation can be targeted to a specific body region (e.g. the face, breasts, buttocks), group of body regions (e.g. lower torso), or the body of a subject as a whole. Regulation of lipofilling activity can include increasing, decreasing, or maintaining lipofilling activity of adipocytes under conditions where lipofilling activity would be normally not be maintained.

In addition to body area, such an approach can also be utilized to identify and characterize compounds that target or otherwise affect or regulate lipofilling activity in subjects according to age.

The present inventors have discovered an in vitro assay to facilitate the identification and characterization of agents demonstrating lipofilling or lipofilling-like activity. It is noted, however, that the present methodology can be applied to numerous systems/activities, and that the present scope is not limited to lipofilling activity. Non-limiting examples can include other aspects of aging, cleansing, vitality, and the like. In one aspect, the method involves exposing replicate cultures of primary human pre-adipocytes, obtained from assorted anatomical sites and subject ages, to various concentrations of test agents during cell differentiation. The cultures are then divided into groups for analysis of lipid accumulation using an assay such as, for example, AdipoRed, cell viability using, for example, Cell Titer Blue, and collection of RNA for gene expression analysis. Expression levels of various genes can then be analyzed to determine the effects of the test agents.

Figure 3:
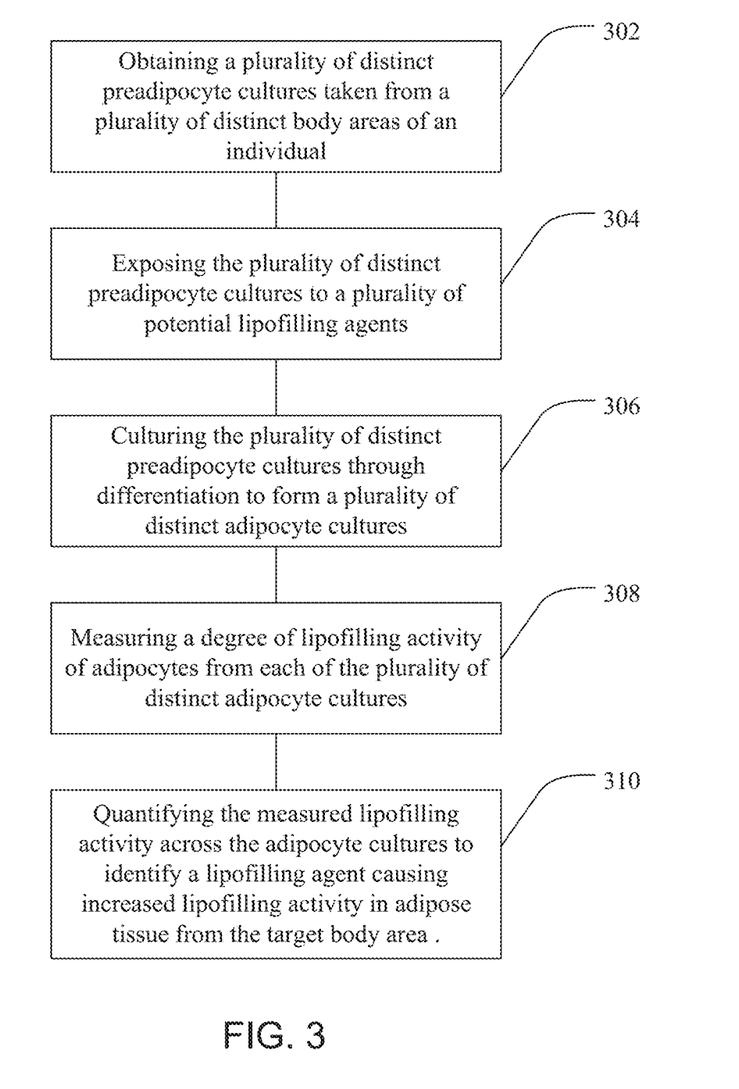
FIG. 3 shows steps of a method for characterizing a lipofilling agent causing increased lipofilling activity in adipose tissue from a target body area compared to adipose tissue from a non-target body area according to another aspect of the present disclosure.

In one aspect, for example, a method is provided for characterizing a lipofilling agent causing increased lipofilling activity in adipose tissue from a target body area compared to adipose tissue from a non-target body area. As is shown in FIG. 3, such a method can include 302 obtaining a plurality of distinct preadipocyte cultures taken from a plurality of distinct body areas of an individual, 304 exposing the plurality of distinct preadipocyte cultures to a plurality of potential lipofilling agents, 306 culturing the plurality of distinct preadipocyte cultures through differentiation to form a plurality of distinct adipocyte cultures, 308 measuring a degree of lipofilling activity of adipocytes from each of the plurality of distinct adipocyte cultures, and 310 quantifying the measured lipofilling activity across the plurality of distinct adipocyte cultures to identify a lipofilling agent causing increased lipofilling activity in adipose tissue from the target body area as compared to adipose tissue in the non-target body area. It is noted that the term "distinct" is intended to refer to the isolated culturing of cells from a specific individual and from a specific body area. In other words, a distinct culture includes cells from only one individual, and from only one body area of that individual. In some examples, however, it may be useful to mix and therefore assay cells in a single culture either from multiple individuals, multiple body areas, multiple ages, or any combination thereof. As such, the present scope includes both distinct and non-distinct culture assays.

In another aspect, a method is provided for characterizing a lipofilling agent that regulates lipofilling activity in adipose tissue from a target body area compared to adipose tissue from a non-target body area. As has been described herein, regulation of lipofilling activity can be an increase in lipofilling activity, a decrease in lipofilling activity, or maintaining lipofilling activity under conditions where lipofilling activity would be normally not be maintained. The method can include obtaining a plurality of distinct preadipocyte cultures taken from a plurality of distinct body areas of an individual, exposing the plurality of distinct preadipocyte cultures to a plurality of potential lipofilling agents, culturing the plurality of distinct preadipocyte cultures through differentiation to form a plurality of distinct adipocyte cultures, measuring a degree of lipofilling activity of adipocytes from each of the plurality of distinct adipocyte cultures, and quantifying the measured lipofilling activity across the plurality of distinct adipocyte cultures to identify a lipofilling agent that regulates lipofilling activity in adipose tissue from the target body area as compared to adipose tissue in the non-target body area.

In addition to obtaining cultures from distinct body areas, in some aspects the plurality of distinct preadipocyte cultures can be obtained from a plurality of individuals of a plurality of ages. The inventors have discovered that preadipocyte cells from the same target area but from individuals of different ages can respond differently to some known lipofilling agents. By including cultures of cells from a number of different ages of individuals in the plurality of distinct preadipocyte cultures, lipofilling agents can be characterized according to age. In this manner, a lipofilling agent composition or regimen can be tailored for individuals of a specific age or age range and for a target body area. In one specific aspect, the plurality of ages of the individuals from which the preadipocyte cultures are taken has an arithmetic range of from 20 years to 60 years. In another aspect the plurality of ages has an arithmetic range of from 20 years to 50 years. In yet another aspect the plurality of ages has an arithmetic range of from 25 years to 35 years. Furthermore, it is additionally contemplated that some aspects can include quantifying the measured lipofilling activity across the plurality of distinct adipocyte cultures to identify a lipofilling agent causing increased lipofilling activity in adipose tissue from individuals of a first age group as compared to individuals of a second age group, wherein the first age group and the second age group are non-overlapping groups. In another aspect, the ages of the first group are greater than the ages of the second group. As one example, the first age group can consist of ages from 40 years old and above. In another example, the first age group can consist of ages from 45 years old and above. In yet another example, the first age group can consist of ages from 50 years old and above.

In addition to age, preadipocyte cultures can be included in the plurality of distinct cultures and thus characterized based on gender, ethnic origin, or any number of different physiological or genetic traits to provide further tailoring options for lipofilling agent compositions.

The target body area can be any region of the body for which lipofilling activity regulation is desired. Non-limiting examples of potential target body areas can include specific body regions (e.g. the face, breasts, buttocks), group of body regions (e.g. lower torso), or the body of a subject as a whole. In one aspect, the target body area can include at least one of the face, breasts, or buttocks. In another aspect, the target body area can be the face. The non-target body area can include any area of the body that is not the target body area, and which also has preadipocytes that show a measurably different response to a potential lipofilling agent as compared to preadipocytes of the target body area.

The measuring of the degree of lipofilling activity can be accomplished by any technique or methodology capable of providing meaningful measurements. For example, lipofilling can be directly assayed by measuring the amount of lipid accumulation in adipocytes. This can be accomplished by a variety of techniques, including visual inspection, dye and fluorescence assays, and the like. Lipofilling can also be assayed somewhat indirectly by measuring the level of gene expression for genes associated with lipofilling activity. Non-limiting examples of possible lipofilling genes can include ABCA12, ACACA, ACLY, ACVR1C, ADIPOQ, ADRB3, AGER///RAGE, AGPATS. AKR1C2, AKR1C3, AKT1, ALDH1A2, APOC1, APOE, APP, AR, ASIP, CASP1, CAV1, CCL2, CD36, CDKN1B, CEBPα, CEBPβ, CEBPδ, CFD, CPT1A, CRABP2, CS, CTBP1, CTNNB1, CYP26A1, CYP26B1, DLK1, E2F1, EGR2///Krox20, ELOVL1, ELOVL3, ELOVL4, ELOVL6, ENC1, ENPEP, ESR1, ESR2, FABP4, FABP5, FAS, FBXW7, FGF2, FGFR1, FGFR2, FOXA2, FOXO4, GATA2, GCGR, GPD1, GSK3B, IGFBP3, IL6, INS, ITGA6, KLF11, KLF15, KLF2, KLF3, KLF4, KLF5, KLF6, KLF7, LEP, LGALS12, LIPE, LMNA, LPIN1, LPL, MAP2K1, MAPK1, MAPK14 (p38), MAPK3, MC2R, MED1, MEF2A, MEF2B, MEF2C, MEF2D, MGLL, NAMPT, NCOA2 (TIF2), NCOR1, NCOR2, NDN, NROB2, NR1H3, NR1H4, NR2F2, PDE3B, PDE5A, PDPK1, PIK3C2A, PIK3C2B, PIK3C2G, PIK3C3, PIK3CA, PIK3CB, PIK3CD, PIK3CG, PIK3R3, PIK3R5, PKC (PRKCA), PLIN1, PLIN2///ADRP (ADFP)/PLIN2, PPARA, PPARD, PPARG, PPARGC1A (PGC-1α), PTGS1, RARA, RARB, RARG, RBP4, RETN, RORA, RXRA, RXRG, S100A1, SCD, SCD2 (SCDS), SERPINA12, SGPP1, SH3PXD2B, SIRT1, SIRT2, SIRT3, SIRT4, SIRT5, SIRT6, SIRT7, SLC2A4///GLUT 4, SOX9, SP-1, SRC, SREBF1, SREBP-2, STAT1, STAT5B, TGFB1, TWIST2, VDR, WNT1, YY1, and the like. Expression of a single gene, multiple genes, or all of the above listed genes, including other examples not listed, can be assayed for lipofilling activity with, for example, Taqman real-time qPCR methods using validated Taqman gene expression assays in an OpenArray format.

In one specific aspect, the effects of three cosmetic ingredients purported to enhance lipid accumulation in adipocytes was evaluated and compared to a positive control represented by a PPAR-gamma agonist, results of which are presented as an example herein. None of the ingredients or vehicle controls differed significantly from each other, with overall responses being highly dependent on the anatomical location for the source of the pre-adipocytes. Lipid production in PPAR-gamma-treated adipocytes was approximately twice or more that of any cosmetic ingredient or vehicle control. In addition, OpenArray analysis revealed that approximately 50% of the genes screened were modulated with expression patterns generally consistent with lipid production.

Prior studies, including the development of agents for generating a certain effect such as, for example, lipofilling of cells in the face, have utilized cell cultures based on ease of acquisition and availability. The present disclosure demonstrates, however, that preadipocytes from different anatomical locations (i.e. body areas) react to such agents very differently. This is further evidenced by the difference in gene expression following exposure to such agents. Furthermore, cell cultures have not been selected based on the age of the donor, which can also be an important factor in determining the efficacy of an agent, as is also described herein. As such, the present disclosure represents a fundamental shift in the thinking and experimental design of active agent assays, including the further development of such actives. As one specific example, the design of an active agent to facilitate lipofilling in facial cells should be designed and tested using preadipocytes from the face. Resulting adipocytes from different anatomical locations may behave differently in response to contact with a given lipofilling agent, and results from such assays and agent designs cannot necessarily be equated to anatomical tissues to which they have not been tested and/or designed.

One benefit that comes with such an understanding relates to the differential effects that can be generated in one tissue type as opposed to another. For example, in the lipofilling of facial adipocytes to reduce signs of aging, targeting facial adipocytes as opposed to thigh or buttock adipocytes can be a great advantage. Conversely, an agent that is developed for the targeted loss of fat in the thighs but not in the face would be highly advantageous. One effect that many people experience during weight loss is the reduction in fat from the body as well as the face. Thus, while an individual may look and feel healthier, the loss of facial fat can also make the individual look older. The loss of weight from particular areas of the body would be preferable, as well as would the overall loss of fat everywhere with the addition of targeted lipofilling in the face.

The targeted loss of weight would also be beneficial to those individuals that carry excess fat in specific regions of the body. In many cases such individuals lose weight from the entire body, and remain with an excess of fat in the specific region, albeit in a lesser amount. Targeted fat removal from such a specific region would complement the overall weight loss to arrive at a more favorable result; the increased fat loss from the specific region as compared to the rest of the body.

Accordingly, the presently disclosed methodology can provide tailored or designer compositions that regulate lipofilling activity based on desired results for specific body areas, and in some cases for specific age groups, gender, ethnic background, and the like. Agents that have activity to facilitate the lipofilling of facial adipocytes, for example, can be discovered and/or verified by assaying potential agents using actual facial adipocytes. In the development of agents that target a specific anatomical region such as the face, potential agents can be tested using facial adipocytes or preadipocytes, as well as cells from other anatomical locations. Potential candidate agents can be identified in such an assay by a positive result from the facial cells and a negative result from cells in one or more of the other anatomical locations.

As has been described, the age of the donor from which the cells have been taken can also be a factor in such assays. Depending on the desired outcome, agents can be tested in one or more age groups. In some aspects, agents can be developed to target a specific age group. This may lead to compositions that are developed for a specific individual demographic. In other cases, the age of the donor can be useful in generating cells with particular response properties that are desirable for a given assay. For example, and as is shown in the example herein, the level of gene expression and the effects of such expression differ between age groups. Cells from younger individuals tend to exhibit lower gene expression, but greater lipofilling, while the opposite trend is true as the age of the individual increases. Additionally, age may be factor that is useful at different stages of agent development. For example, it may be beneficial in some cases to utilize cells from an older individual for in assays where the increased gene expression is important. In other cases, it can also be beneficial to utilize cells from a population that may be most affected, or in some cases more sensitive to, a given effect such as the loss of facial fat causing an apparent older appearance.

Accordingly, in another aspect a method is provided for the assaying of agents for desired effects in specific tissues or cell types. Such a method can include culturing cells from the specific tissues or cell types, and exposing the cultures to one or more test agents. The cell cultures can then be assayed for the desired effects. It is likely that such effects would thus translate to the specific tissues or cell types in an individual to which a candidate agent is given. Additionally, the method can include assaying gene expression in the cell cultures as a result of exposure to the test agents, thus providing a genetic assessment of the desired effect in the specific tissues or cell types. The method can also include positive and/or negative controls to further evaluate potential candidates. Cultures can also be tested for cytotoxicity.

In another specific aspect, a method is provided for assaying agents for lipofilling and/or lipofilling-like behavior in facial preadipocyte cells. Such a method can include culturing facial preadipocytes taken from the facial tissue of an individual, exposing the facial preadipocytes to one or more potential lipofilling agents, culturing the facial preadipocytes, and quantifying the cultures for lipofilling and/or lipofilling-like behavior. In some aspects, the preadipocytes can be cultured until they mature into adipocytes before quantifying for lipofilling and/or lipofilling-like behavior. In one specific aspect, quantifying includes assaying the cultured cells for the amount of lipid stored therein. In another specific aspect, quantifying includes assaying the level of gene expression in cultured cells to determine the activity of genes associated with lipofilling. In yet another specific aspect, quantifying includes both assaying the amount of lipid stored and the level of gene expression.

EXAMPLES

The following is an example of the applicability of standard in vitro cell culture methods for screening topical cosmetic ingredients for use in supporting the maintenance or enhancement of adipocyte number and lipid in the subcutis. A comprehensive in vitro approach is used to evaluate cosmetic ingredients.

Primary human preadipocytes are obtained from individual subjects from Zen-Bio, Inc. The cells are cultured to confluence in 96-well plates (for lipid accumulation and toxicity assessments) and in 12-well plates (for RNA isolation) using Preadipocyte Medium (Zen-Bio, Cat. #PM-1). Preadipocytes are induced to differentiate into adipocytes for seven days with Adipocyte Differentiation Medium (Zen-Bio Cat. #DM-2), in the presence or absence of test compounds or controls (described in the figures below). After seven days, the differentiation medium and compounds is removed and replaced with Adipocyte Maintenance Medium (Zen-Bio, Cat. #AM-1) and the cells are allowed to continue differentiation for an additional seven days.

Cultures are treated with each test compound or controls in triplicates. Each compounds, including controls, is examined for compound toxicity using Cell Titer Blue (Promega, Cat. #TB317), and for lipid accumulation using AdipoRed (Lonza, Cat. #7009). Compound toxicity (viability) is assessed by adding 5 µL of the Cell Titer Blue reagent to each well containing 100 µL medium. After 2-hour incubation at 37° C., compound toxicity is measured by fluorescence using excitation/emission wavelengths of 560/590 nm.

For lipid assessment by AdipoRed, the medium is removed from the cultures and the cells are rinsed with phosphate-buffered saline (PBS). Cells are incubated with AdipoRed (5 µL) in PBS (200 µL) for 15 minutes at room temperature. Fluorescence is then read for each well using excitation/emission wavelengths of 485/535 nm respectively.

Cultures are collected for RNA isolation after differentiation by first removing the culture medium and rinsing with PBS. After removing the PBS wash, the cells are lysed using 350 μL Buffer RLT (Qiagen) containing 10 μL/mL β-mercaptoethanol. The resulting cell lysates are transferred to storage tubes, immediately frozen using a dry ice/isopropanol bath and stored at −80° C. for subsequent analysis. RNA is isolated using RNeasy mini kits following the manufacturer's instructions for cultured cells (Qiagen). RNA concentration and purity are determined using a Nanodrop 2000 spectrophotometer.

cDNA is generated and preamplified using a TaqMan Custom PreAmp Pool and a SuperScript VILO cDNA Synthesis Kit and TaqMan PreAmp Master Mix, respectively, according to the manufacturer's instructions (Life Technologies). The preamplification reaction is run for 10 cycles.

qPCR reactions are run using validated gene expression assays in an OpenArray format, which are run in a QuantStudio 12K Flex instrument. All genes are assayed in duplicate. Data are analyzed by RealTime StatMiner software v4.2 for statistical analysis using the relative quantification (RQ) method (gene expression changes expressed relative to untreated control sample).

Figure 4:
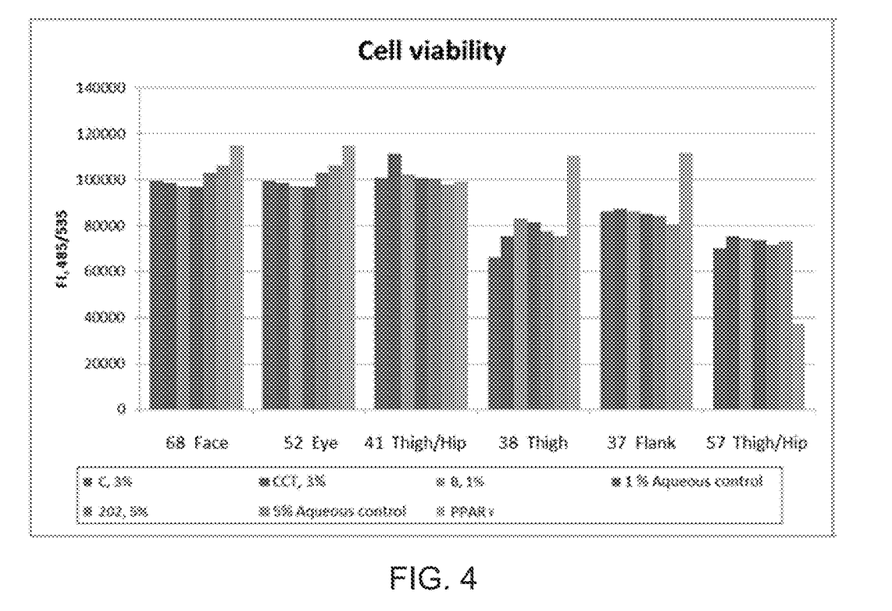
FIG. 4 shows data representing cell viability in cultured cells according to another aspect of the present disclosure.

Preadipocytes from six individual female donors were used to initially assess for compound cytotoxicity of three cosmetic ingredients (B, C, 202), three vehicle controls (5% water, 1% water, and caprylic/capric triglyderide, CCT), and a positive control (PPARγ agonist). Details regarding the preadipocytes are shown in Table 1. The preadipocytes were isolated from differing anatomical sites and varied by age. Compound toxicity (cell viability) was measured for each compound and controls using Cell Titer Blue as described. None of the compounds or controls induced cytotoxicity in human preadipocytes (FIG. 4). Depending on a donor, PPARγ agonist induced slight stimulation of preadipocyte viability.

TABLE 1

| Age | Anatomical Site | BMI |
| --- | --- | --- |
| 37 | Flank | 23.5 |
| 38 | Thigh | 20.4 |
| 41 | Thigh/Hip | 20.9 |
| 52 | Eye | 22.2 |
| 57 | Thigh/Hip | 23.9 |
| 68 | Face | 24.4 |

Figure 5:
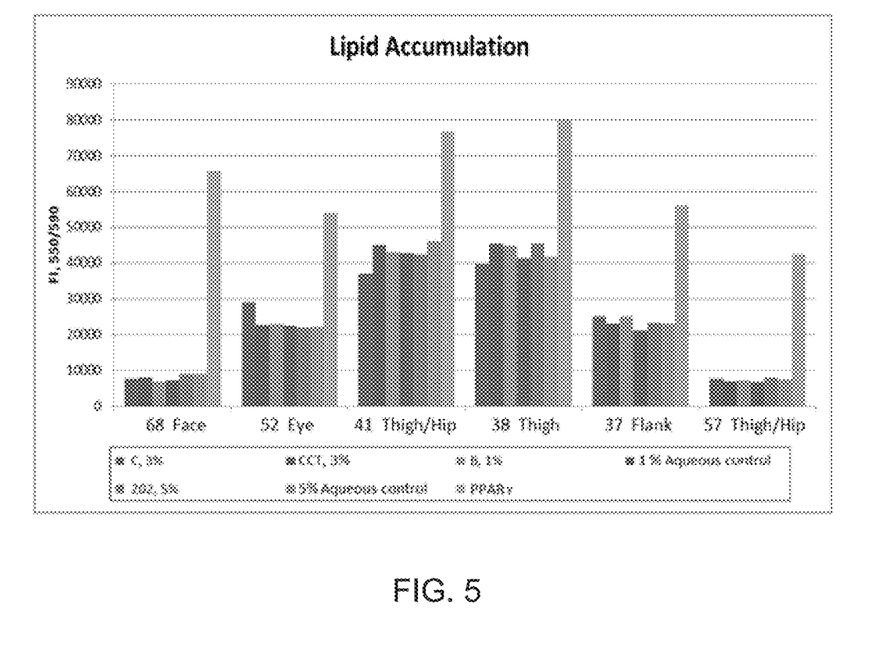
FIG. 5 shows data representing lipid accumulation in cultured cells according to another aspect of the present disclosure.

The same set of donor cultures were dosed with the same test compounds and controls, and were subsequently evaluated for lipid accumulation. Lipid accumulation was measured for each compound and controls using AdipoRed as described. The results reveal significant variation in the lipid accumulation potential of differentiating preadipocytes from donors of different age and anatomical sites (FIG. 5). All preadipocytes responded well to PPARγ agonist, suggesting the lipid production capacity is fully functional in the presence of strong stimulation. None of the cosmetic ingredient test agents produced significantly more lipid accumulation than their vehicle controls.

Figure 6:
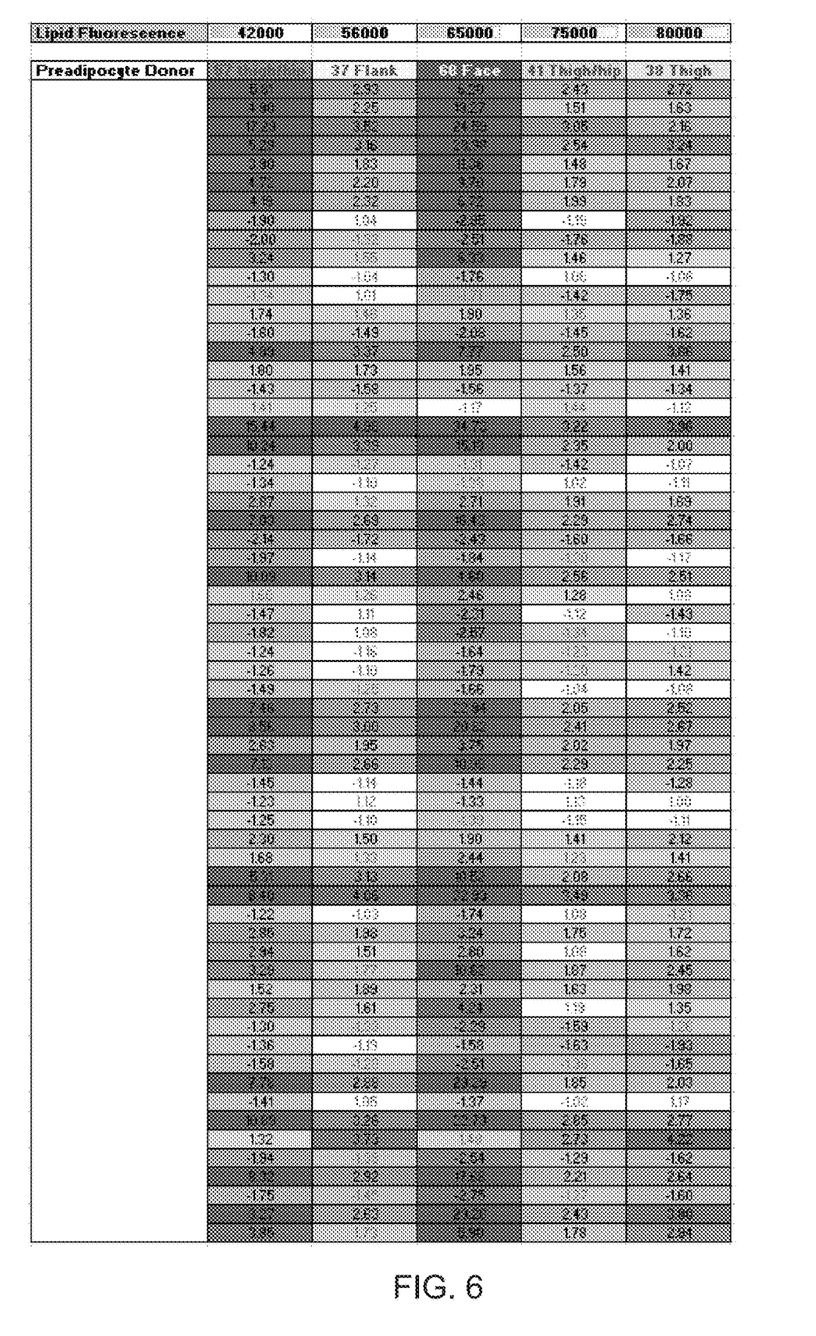
FIG. 6 shows data representing gene expression in cultured cells according to another aspect of the present disclosure.

These preadipocytes were further investigated for expression of 152 genes believed to be involved in lipid production and metabolism. Preadipocyte cultures were dosed with the same compounds and controls at the same time as other assays for correlation analysis. Based on the gene expression analysis results, older preadipocytes modulated their gene expression more intensely with lesser lipid accumulation (FIG. 6). In other words, younger preadipocytes modulated their gene expression with less intensity, but accumulated more total lipid. This suggests that older cells are likely trying to compensate for less efficient protein synthesis activities involved in lipid production. Gene expression was modulated more strongly in 57 and 68 years old subjects, with less lipid accumulation. However, PPARγ data from the 52 years old eye sample did not show any significant modulation of gene expression. FIG. 6 shows selective gene expression data 14 days after differentiation initiation (7 days without PPARγ agonist). These genes are involved in lipid production, lipid metabolism, preadipocyte differentiation, etc. The top row shows lipid accumulation level for the each sample, as well as the age and location of the source of each set of isolated preadipocytes. In the spreadsheet, red cells indicate stimulation and blue cells indicate inhibition of gene expression, with cell color intensity indicating stronger modulation. In addition, the fold inhibition is shown as negative numbers, while fold stimulation is shown as a positive number. Grey colored cells indicate statistically non-significant modulation.

Younger samples (37, 38 & 41 years old) accumulated more lipids, with less modulation of gene expression. Only one sample from the face exhibited greater stimulation or inhibition of gene expression, and was the oldest preadipocytes in this study. PPARγ stimulated gene expression much more than cosmetic actives, as suspected from lipid production data. Not much gene expression modulation was observed with cosmetic compounds and their vehicle controls, however we cannot rule out the inappropriate timing for the gene expression analysis although, likely due to its potency, PPARγ stimulated preadipocytes retained gene expression modulation capacity even 7 days after the removal of PPARγ agonist in the media.

The example provides evidence that the methods described can be used to identify test agents with lipofilling activity. Variation imparted by differences in preadipocytes obtained from different donors and anatomical sites suggests that, to avoid inter-study variability, tissue used for the isolation of preadipocytes should be from subjects of the same sex, and from a similar anatomical site, and from a similar age range.

Further, gene expression analyses show that, although preadipocytes obtained from tissue of differing locations and from subjects of differing ages, the ability to produce lipid was retained for all cell samples given a strong enough stimulus, in this case with the PPARγ agonist.

Based on these results, it appears that the efficiency of proteins involved in lipid accumulation is reduced with age, and that cells are likely trying to adapt or to compensate by excessively modulating gene expression, even more so in facial samples.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

We claim:

1. A method for characterizing a lipofilling agent causing increased lipofilling activity in adipose tissue from a target body area compared to adipose tissue from a non-target body area, comprising:

obtaining a plurality of distinct natural preadipocyte cultures taken from a plurality of distinct body areas of a plurality of individuals of a plurality of ages;
exposing the plurality of distinct natural preadipocyte cultures to a plurality of potential lipofilling agents;
culturing the plurality of distinct natural preadipocyte cultures through differentiation to form a plurality of distinct natural adipocyte cultures;
measuring a degree of lipofilling activity of natural adipocytes from each of the plurality of distinct natural adipocyte cultures; and
quantifying the measured lipofilling activity across the plurality of distinct natural adipocyte cultures to identify a lipofilling agent causing increased lipofilling activity in adipose tissue from the target body area as compared to adipose tissue in the non-target body area and causing increased lipofilling activity in adipose tissue from individuals of a first age group as compared to individuals of a second age group, wherein the first age group and the second age group are non-overlapping groups.

2. The method of claim 1, wherein the plurality of ages consists of ages greater than or equal to 20 years of age and less than or equal to 60 years of age.

3. The method of claim 1, wherein the plurality of ages has an arithmetic range of from 20 years to 50 years.

4. The method of claim 1, wherein the plurality of ages has an arithmetic range of from 25 years to 35 years.

5. The method of claim 1, wherein the ages of the first group are greater than the ages of the second group.

6. The method of claim 5, wherein the first age group consists of ages 40 and above.

7. The method of claim 6, wherein the first age group consists of ages 45 and above.

8. The method of claim 1, wherein the target body area includes a region selected from the group consisting of face, breasts, and buttocks.

9. The method of claim 1, wherein the target body area is face.

10. The method of claim 1, wherein measuring the degree of lipofilling activity includes measuring an amount of accumulated lipid in the natural adipocytes.

11. The method of claim 1, wherein measuring the degree of lipofilling activity includes measuring a level of gene expression in the natural adipocytes associated with lipofilling activity.

\* \* \* \* \*